United States Patent
Cabaj et al.

(10) Patent No.: US 7,321,064 B1
(45) Date of Patent: Jan. 22, 2008

(54) PREPARATION OF AMIDES OF RETINOIC ACID VIA MIXED ANHYDRIDE AND MIXED CARBONATE INTERMEDIATES

(75) Inventors: John E. Cabaj, Sheboygan, WI (US); Jeff J. Hutchison, Sheboygan, WI (US)

(73) Assignee: Cedarburg Pharmaceuticals, Inc., Grafton, WI (US)

( * ) Notice: Subject to any disclaimer, the term of this patent is extended or adjusted under 35 U.S.C. 154(b) by 0 days.

(21) Appl. No.: 11/715,571

(22) Filed: Mar. 8, 2007

(51) Int. Cl.
 *C07C 231/00* (2006.01)
(52) U.S. Cl. .................................... 564/133
(58) Field of Classification Search ............ None
 See application file for complete search history.

(56) References Cited

U.S. PATENT DOCUMENTS

| | | |
|---|---|---|
| 4,108,880 A | 8/1978 | Gander et al. |
| 4,190,594 A | 2/1980 | Gander et al. |
| 4,323,581 A | 4/1982 | Gander |
| 4,556,518 A | 12/1985 | Lucci |
| 4,665,098 A | 5/1987 | Gibbs et al. |
| 5,399,757 A | 3/1995 | Maryanoff |
| 5,985,292 A | 11/1999 | Fourneron et al. |
| 6,133,463 A | 10/2000 | Fourneron et al. |
| 6,551,605 B2 | 4/2003 | Bonda |
| 7,169,813 B2 | 1/2007 | Formelli |
| 7,169,819 B2 | 1/2007 | Gupta et al. |

OTHER PUBLICATIONS

Hong S. Sin et. al., "Synthesis and Preliminary Biological Studies of Novel Retinamide Derivatives", Bull. Korean Chem. Soc., vol. 23, No. 12, pp. 1806-1810, 2002.
Sangmam et. al., "A Simple, General and Efficient Method for O and N-Retinoylation", Synthetic Communications 28(16), pp. 2945-2958, 1998.

*Primary Examiner*—Paul A. Zucker
(74) *Attorney, Agent, or Firm*—Quarles & Brady LLP

(57) ABSTRACT

Processes for preparing amides of retinoic acid are disclosed. Intermediates useful in the preparation of amides of retinoic acid are also disclosed. In one version of the invention, fenretinide is produced via activation of retinoic acid (tretinoin) via its corresponding mixed anhydride or mixed carbonate followed by reaction of the activated intermediate with 4-aminophenol. Other amides of retinoic acid and isomers of retinoic acid, such as the 9-cis-form or 13-cis-form can also be made by this invention.

19 Claims, 2 Drawing Sheets

PREPARATION OF AMIDES OF RETINOIC ACID VIA MIXED ANHYDRIDE AND MIXED CARBONATE INTERMEDIATES

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

1. Field of the Invention

The invention relates to processes for preparing amides of retinoic acid. In particular, the invention provides a procedure for producing N-(4-hydroxyphenyl)retinamide (fenretinide) on a production scale. In one version of the invention, fenretinide is produced via activation of retinoic acid (tretinoin) via its corresponding mixed anhydride or mixed carbonate followed by reaction of the activated intermediate with 4-aminophenol. Other amides of retinoic acid and isomers of retinoic acid, such as the 9-cis-form (alitretinoin) or 13-cis-form (isotretinoin), are also known to have useful properties and can be made by this invention.

2. Description of the Related Art

Fenretinide (CAS# 65646-68-6) is currently in Phase I clinical trials for the treatment of childhood brain cancer. Previous syntheses of fenretinide involved the activation of retinoic acid with $PCl_3$ (see FIG. 1 and U.S. Pat. No. 4,190,594 to Gander et al.), with $SOCl_2$ (see Hong S. Sin et al., "Synthesis and Preliminary Biological Studies of Novel Retinamide Derivatives", *Bull. Korean Chem. Soc.*, Vol. 23, No. 12, pages 1806-1810, 2002), and with N,N'-Dicyclohexyl-carbodiimide (DCC) (see Sangmam et al., "A Simple, General and Efficient Method for O and N-Retinoylation", *Synthetic Communications* 28(16), pages 2945-2958, 1998).

Another process has been developed in which retinoic acid is first activated as the acid chloride using the Vilsmeier reagent (dimethylchloro-formamidinium chloride). The acid chloride is then added to bis-(N, O)-trimethylsilyl-p-aminophenol (See FIG. 2 and U.S. Pat. No. 5,399,757 to Maryanoff).

However, these methods can be unsuitable for scale-up and therefore, there is a need for simpler, scaleable, and less expensive processes for preparing amides of retinoic acid such as fenretinide.

SUMMARY OF THE INVENTION

The foregoing needs are met by a process according to the invention for preparing amides of retinoic acid. The invention provides simpler, scalable and less expensive processes for preparing the amides of retinoic acid such as fenretinide.

In one version of the invention, fenretinide is produced via activation of retinoic acid (tretinoin) via its corresponding mixed anhydride followed by reaction of the activated intermediate with 4-aminophenol. In another version of the invention, fenretinide is produced via activation of retinoic acid (tretinoin) via its corresponding mixed carbonate followed by reaction of the activated intermediate with 4-aminophenol. Other amides of retinoic acid and isomers of retinoic acid, such as the 9-cis-form (alitretinoin: CAS# 5300-03-8) or 13-cis-form (isotretinoin: CAS# 4759-48-2), can be made by this invention.

In one aspect, the invention provides a process for preparing an amide of retinoic acid. In the process, a retinoic acid having the formula:

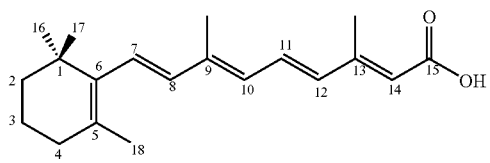

or isomers thereof is reacted with a compound having a formula selected from:

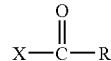

and

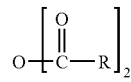

wherein R is alkyl or aryl or alkoxy, and X is a halogen, to produce an intermediate having the formula:

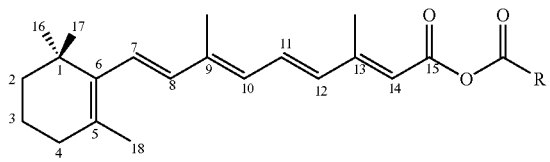

The alkyl or alkoxy of the R group may be straight chain or branched, and the alkyl or aryl or alkoxy of the R group may be substituted or unsubstituted. The intermediate is then reacted with 4-aminophenol to produce an amide of retinoic acid having the formula:

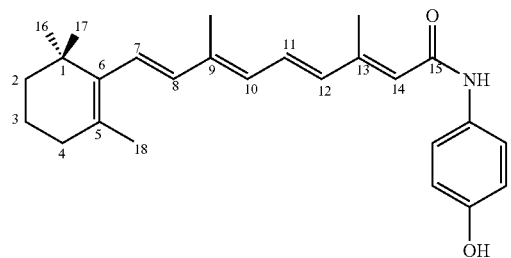

or isomers thereof. The amide may be prepared in a yield of at least 70%, and preferably the amide is prepared in a yield of at least 85%, and most preferably the amide is prepared in a yield of at least 95%.

In the process, the retinoic acid may be all-trans-retinoic acid, 9-cis-retinoic acid, 13-cis-retinoic acid or another isomer of retinoic acid. In the compound that is reacted with the retinoic acid, X may be chlorine, and R may be trimethylalkyl such as —C(CH₃)₃, or —C(CH₃)₂CH₂CH₃, or —OCH(CH₃)₂, or —OCH₂CH(CH₃)₂. In one example process of the invention, the compound is trimethylacetyl chloride or 2,2-dimethylbutyryl chloride. In another example process of the invention, the compound is isobutylchloroformate or isopropylchloroformate.

The retinoic acid and the compound may be reacted in the temperature range of 0-10° C. in the presence of a solvent selected from the group consisting of ethyl acetate, t-butyl methyl ether, 2-methyltetrahydrofuran, toluene, acetonitrile, methylene chloride, dimethyl formamide, tetrahydrofuran, pyridine, and mixtures thereof. Also, the retinoic acid and the compound may be reacted in the temperature range of 0-10° C. in the presence of an amine base, or a base selected from the group consisting of triethylamine, diisopropylethylamine, N-methylmorpholine, pyridine, 1,8-diazabicyclo [5.4.0]undec-7-ene, metal carbonates, metal bicarbonates, and mixtures thereof. The intermediate may be reacted with 4-aminophenol in the temperature range of 0-10° C. in the presence of a solvent selected from the group consisting of pyridine, dimethyl formamide, dimethylacetamide, and mixtures thereof.

In one example embodiment, the invention provides a process to produce fenretinide via the t-butyl mixed anhydride of retinoic acid. In another example embodiment, the invention provides a process to produce fenretinide via the 2,2-dimethylbutyryl mixed anhydride of retinoic acid. In yet another example embodiment, the invention provides a process to produce fenretinide using other mixed anhydrides of retinoic acid.

In one example embodiment, the invention provides a process to produce fenretinide via an isobutyl mixed carbonate of retinoic acid. In another example embodiment, the invention provides a process to produce fenretinide via the isopropyl mixed carbonate of retinoic acid. In yet another example embodiment, the invention provides a process to produce fenretinide using other mixed carbonates of retinoic acid.

In another aspect, the invention provides a compound having the formula:

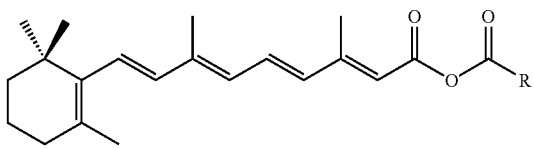

or isomers thereof, wherein R is alkyl or aryl or alkoxy with the proviso that R is not tertiary butyl. The alkyl or alkoxy of the R group may be straight chain or branched, and the alkyl or aryl or alkoxy of the R group may be substituted or unsubstituted. In the compound, R may be trimethylalkyl such as —C(CH₃)₃, or —C(CH₃)₂CH₂CH₃, or —OCH(CH₃)₂, or —OCH₂CH(CH₃)₂. The compound may be in various isomeric forms such as the all-trans form, the 9-cis-form, the 13-cis-form and the like.

In one example embodiment, the invention provides a t-butyl mixed anhydride intermediate of retinoic acid wherein the intermediate of retinoic acid may be in various isomeric forms such as the all-trans form, the 9-cis-form, the 13-cis-form and the like. In another example embodiment, the invention provides a novel 2,2-dimethylbutyryl mixed anhydride intermediate of retinoic acid wherein the intermediate of retinoic acid may be in various isomeric forms such as the all-trans form, the 9-cis-form, the 13-cis-form and the like.

In one example embodiment, the invention provides a novel isobutyl mixed carbonate of retinoic acid wherein the intermediate of retinoic acid may be in various isomeric forms such as the all-trans form, the 9-cis-form, the 13-cis-form and the like. In another example embodiment, the invention provides a novel isopropyl mixed carbonate of retinoic acid wherein the intermediate of retinoic acid may be in various isomeric forms such as the all-trans form, the 9-cis-form, the 13-cis-form and the like.

These and other features, aspects, and advantages of the present invention will become better understood upon consideration of the following detailed description, drawings, and appended claims.

DETAILED DESCRIPTION OF THE INVENTION

Figure 1:
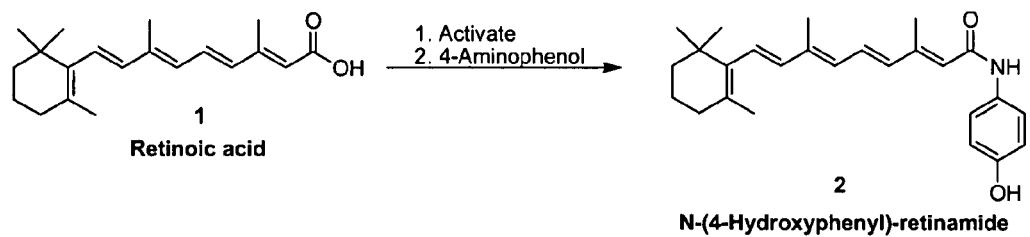
FIG. 1 shows a prior art reaction scheme for preparing fenretinide.
Figure 2:
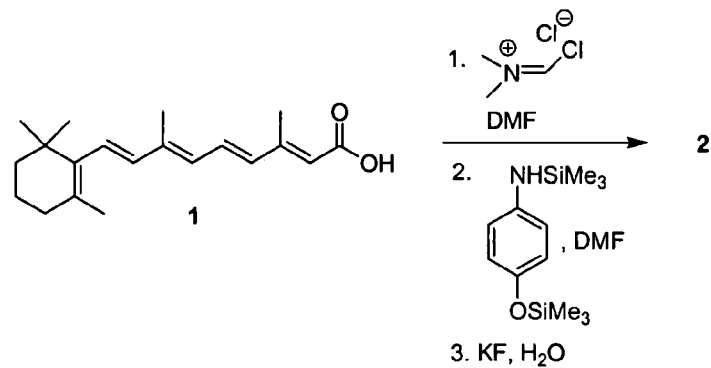
FIG. 2 shows another prior art reaction scheme for preparing fenretinide.
Figure 3:
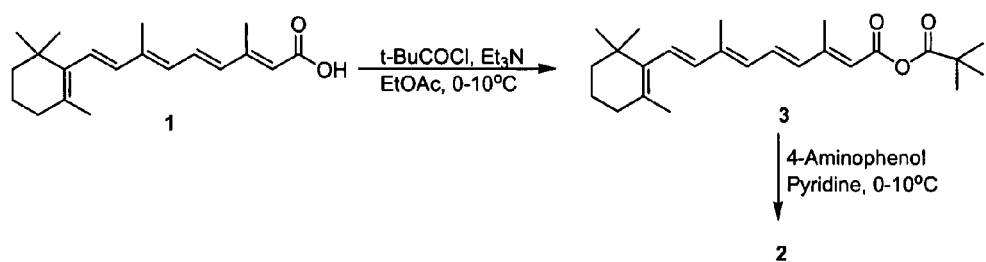
FIG. 3 shows a reaction scheme for preparing fenretinide according to one version of the invention.

This invention provides processes for preparing amides of retinoic acid. In one example scheme depicted in FIG. 3, the invention provides a cost effective, safe, and scaleable process to prepare fenretinide 2. Activation via a mixed anhydride meets these requirements. The t-butyl mixed anhydride 3 of retinoic acid was prepared by adding trimethylacetyl chloride (t-BuCOCl), which has the formula (CH₃)₃CCOCl, to a suspension of retinoic acid 1 and triethylamine (Et₃N) in ethyl acetate (EtOAc) at a temperature of about 0-10° C.

Other solvents such as t-butyl methyl ether, 2-methyltetrahydrofuran, toluene, acetonitrile, methylene chloride, and pyridine can also be used. Other bases such as diisopropylethylamine, and similar amine bases can be used in the activation step as well. Other inorganic bases such as metal carbonates and metal bicarbonates may be used. Non-limiting examples of metal carbonate bases include alkali carbonates such as Li₂CO₃, Na₂CO₃, K₂CO₃, and Cs₂CO₃, and non-limiting examples of metal bicarbonate bases include alkali bicarbonates such as NaHCO₃ and KHCO₃. Other anhydrides such as that formed with 2,2-dimethylbutyryl chloride, which has the formula CH₃CH₂(CH₃)₂COCl, can also be used to form similar mixed anhydrides that can be used in the coupling.

In another step, 4-aminophenol is added to the mixed anhydride as a pyridine suspension at about 0-10° C. The reaction is allowed to stir for a period of time to allow for reaction completion and then worked up with subsequent HCl, K₂CO₃, and brine washes. The organic solution is dried, concentrated, and crystallized from ethyl acetate/heptane to give fenretinide as a bright crystalline solid in about 70-93% yield (98-99 area percent purity by HPLC). The 4-aminophenol can also be added as a dimethyl formamide (DMF) or dimethylacetamide suspension. The crude product can be recrystallized from ethanol and water to give recrystallized fenretinide in about 85-90% recovery with a purity of greater than 99% by area percent HPLC.

Figure 4:
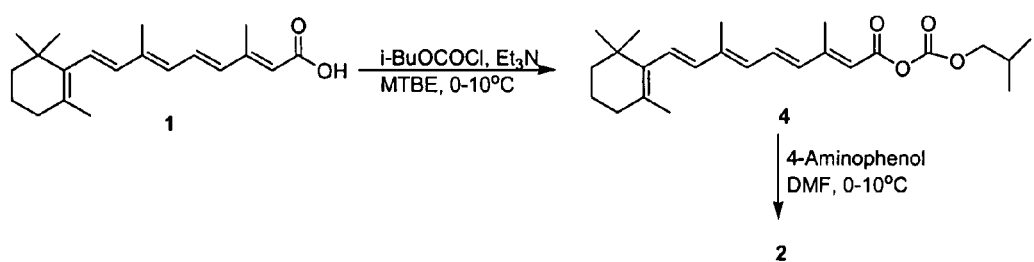
FIG. 4 shows a reaction scheme for preparing fenretinide according to another version of the invention.

In another example scheme depicted in FIG. 4, the invention provides a cost effective, safe, and scaleable process to prepare fenretinide. In this version, the isobutyl carbonate of retinoic acid can be used to produce fenretinide. In this case isobutylchloroformate (i-BuOCOCl), which has the formula $(CH_3)_2CHCH_2OCOCl$, is added to a t-butyl methyl ether (MTBE) slurry of retinoic acid 1 and triethylamine at about 0-10° C. Other solvents such as tetrahydrofuran (THF), ethyl acetate, DMF, and toluene can also be used. Other bases such as metal carbonates, metal bicarbonates, diisopropylethylamine, N-methylmorpholine, pyridine, 1,8-diazabicyclo[5.4.0]undec-7-ene (DBU—CAS # 6674-22-2), and similar bases can be used instead of triethylamine. Other mixed carbonates such as that formed with isopropylchloroformate, which has the formula $(CH_3)_2CHOCOCl$, can also be used in the coupling. After the activation is complete, the 4-aminophenol is added to the mixed carbonate 4 as a suspension in DMF. After reaction completion, the crude fenretinide is isolated as in the case of the mixed anhydride procedure to give fenretinide 2 in 70-85% yield (98-99 area percent purity). The 4-aminophenol can also be added as a DMF or pyridine suspension. The 4-aminophenol can also be protected as the trimethylsilyl ether and used in the coupling.

EXAMPLES

The following examples serve to further illustrate the invention and are not intended to limit the invention in any way.

Example 1

Preparation of the T-Butyl Mixed Anhydride of Retinoic Acid

To a 100 milliliter round bottom flask was added 2.00 grams (6.67 mmol) of retinoic acid and 40 milliliters of t-butyl methyl ether. The slurry was cooled to a bath temperature of about 0-10° C. To the slurry was added 1.02 milliliters (7.40 mmol) of triethylamine via syringe over about 1 minute. Trimethylacetyl chloride (0.86 milliliters, 7.0 mmol) was then added via syringe over about 10 minutes. The bright yellow slurry was then stirred for 3 hours at a bath temperature of about 0-10° C. and then held overnight in a refrigerator. The next day the reaction mixture was filtered, the filtered solids were washed thoroughly with t-butyl methyl ether, and the filtrate was concentrated via rotary evaporation (about 35-40° C. external temperature) to give 2.84 grams of the mixed anhydride as a gold oil. The NMR and IR of the oil corresponded to the assigned structure (t-butyl mixed anhydride of retinoic acid). The presence of residual solvent was evident from the NMR.

Example 2

Preparation of Fenretinide Via the T-Butyl Mixed Anhydride of Retinoic Acid

To a 5-Liter 4 neck round bottom flask equipped with a mechanical stirrer, temperature probe, addition funnel, and nitrogen inlet adapter was added 100.0 grams (333.3 mmol) of retinoic acid and 1.0 liter of ethyl acetate (EtOAc). The slurry was cooled to an internal temperature of 5° C. Triethylamine (50.7 milliliters, 366 mmol) was added all at once via graduated cylinder. To the thin slurry was then added trimethylacetyl chloride (45.1 milliliters, 366 mmol) via addition funnel over about 23 minutes at an internal temperature of less than 5° C. After 3.5 hours, the reaction was judged to be complete by HPLC analysis. To the bright yellow slurry of the mixed anhydride was added a thin suspension of 4-aminophenol (76.3 grams, 700 mmol) in 500 milliliters of pyridine over 30 minutes at an internal temperature of 3-5° C. After 2 hours, the reaction was judged to be complete by HPLC analysis. To the slurry was added 500 milliliters of water over 10 minutes at an internal temperature of 4-8° C. After stirring for 30 minutes the layers were separated and the aqueous layer was extracted with 500 milliliters of EtOAc. The combined organic layers were washed with 3M HCl (3×700 milliliters). The pH of the last wash was 1-2 as determined by pH paper. The organic layer was then washed with 30% aqueous $K_2CO_3$ (3×600 milliliters) and brine (2×600 milliliters). The organic layer was held overnight at 0-10° C. The next morning the solution was dried with 50 grams of $Na_2SO_4$. After filtration of the drying salts, the amber solution was concentrated to a final volume of about 250 milliliters via rotary evaporation at an external temperature of 45-50° C. The thick slurry was allowed to cool to ambient temperature and 700 milliliters of heptane was added via addition funnel over about 45 minutes. The slurry was cooled to an internal temperature of 0-5° C. and held at this temperature for about 2 hours. The slurry was filtered and washed with a 0-10° C. 5/1 (v/v) mixture of heptane/EtOAc (1×200 milliliters, 1×150 milliliters) to give 161 grams of crude fenretinide wet cake (LOD=25%, 93% yield based on LOD, 98% pure by area percent).

To a 5-liter 4-neck round bottom flask equipped with a mechanical stirrer, reflux condenser, and temperature probe was charged 154.2 grams of crude fenretinide wet cake (115.6 grams contained fenretinide). The flask was charged with 925 milliliters (8 milliliters/gram) of ethanol and the mixture heated to >70° C. To the amber/orange solution, 500 milliliters (4.3 milliliters/gram) of distilled water was added drop wise over 50 minutes while maintaining a temperature of >70° C. After the addition the heat was turned off and the solution cooled to room temperature with stirring. As the solution cooled the product began to crystallize as a yellow solid. The suspension was cooled to 30-35° C. and then further cooled to 0-5° C. with the aid of an ice-water bath. The suspension was stirred at 0-10° C. for two hours and filtered. The yellow solids were washed two times with 250 milliliters of cold 3:1 (v/v) of $H_2O$/ethanol. The solids were dried a short time on the filter. The product was dried over the weekend at 30-40° C. in the drying oven under vacuum to give 97.6 grams of product as a yellow crystalline solid (84% recovery, 79% overall yield from retinoic acid, 99.6% pure by area percent HPLC).

Example 3

Preparation of Fenretinide Using 2,2-Dimethylbutyrichloride

To a 250 milliliter round bottom flask was charged 2.00 grams (6.67 mmol) of retinoic acid and 20 milliliters of $CH_3CN$. The slurry was cooled to an external temperature of 0-10° C. while 1.0 milliliters of $Et_3N$ (7.3 mmol) was charged via syringe. To the slurry was added 0.96 milliliters (7.0 mmol) of 2,2-dimethylbutyrichloride via syringe over about 10 minutes. A thick, unstirrable slurry formed. Ten milliliters of additional $CH_3CN$ was added to improve the stirring. After about 3.5 hours, the activation was judged to be complete by HPLC analysis. To the slurry was added 2.0 milliliters of pyridine via syringe. 4-aminophenol (1.53 grams, 14.0 mmol) was then added as a solid in 2 portions over about 15 minutes. After stirring for 2 hours, the reaction was held overnight in the refrigerator (about 0-10° C.). The following morning the reaction was judged to be complete by HPLC analysis. At an external temperature of 0-10° C., 20 milliliters of 3M HCl was added dropwise over about 15 min. After stirring for about 15 minutes, about 20 milliliters of solvent was removed via rotary evaporation (45° C. bath temperature). The slurry was filtered, washed twice with 10 milliliters of water and once with 15 milliliters of heptane. The dark brown solid was dried at about 40° C. overnight on a high vacuum pump to give 2.52 grams of fenretinide (97% yield, 97% pure by area, 1.4% retinoic acid).

Example 4

Preparation of the Isobutyl Mixed Carbonate of Retinoic Acid

To a 500 milliliter 4-neck bottom flask equipped with a mechanical stirrer, temperature probe, and nitrogen inlet adapter was added 20.0 grams (66.7 mmol) of retinoic acid and 200 milliliters of THF. The solution was cooled to an internal temperature of 5° C. and 11.8 milliliters (85.3 mmol) of triethylamine was added via addition funnel over about 1 minute. Isobutylchloroformate (10.0 milliliters, 73.2 mmol) was then added via the addition funnel at 4-7° C. over 20 minutes. The resulting slurry was then stirred for about 3 hours (0-20° C.) at which point the reaction was judged to be complete by HPLC analysis. The slurry was cooled to an internal temperature of 5° C. and 50 milliliters of water was added drop wise at an internal temperature of 8-11° C. The layers were then separated and the aqueous layer was extracted with t-butyl methyl ether (2×70 milliliters). The combined organic layers were washed with water (2×60 milliliters), dried over Na$_2$SO$_4$, and concentrated via rotary evaporation to give 28.3 grams of the mixed carbonate as a light brown oil (97% pure by area percent HPLC). TLC analysis after workup indicated that a certain amount of hydrolysis had occurred during the workup. The NMR of the crude product corresponded to the assigned structure (isobutyl mixed carbonate of retinoic acid) and included peaks corresponding to t-butyl methyl ether.

Example 5

Preparation of Fenretinide Via the Isobutyl Mixed Carbonate of Retinoic Acid

All-trans-retinoic acid 5.0 grams (0.0166 mol) was charged to a 250 milliliter round bottom flask, followed by 100 milliliters of methyl-t-butyl ether (MTBE) and the stirrer started. The resulting suspension was cooled to <10° C., 5.8 milliliters (0.0417 mol) of triethylamine was added and the mixture was further cooled to <5° C. While maintaining a temperature of less than 5° C., 2.5 milliliters (0.0183 mol) of isobutylchloroformate was added drop wise over approximately fifteen minutes. The resulting yellow suspension was stirred for 1 hour at which point the reaction was shown to be complete via HPLC analysis. A hazy solution of 2.73 grams (0.025 mol) of 4-aminophenol in 12 milliliters of DMF was added to the mixed carbonate over 10 minutes at less than 10° C. The reaction was again stirred for 1 hour and checked for completion by HPLC. After 1 hour the reaction was 97% complete with 9% retinoic acid regenerated. The reaction was stirred one additional hour and then quenched with 25 milliliters of aqueous 3M HCl at <10° C. The layers were separated and the aqueous phase re-extracted with 50 milliliters of MTBE. The combined organic extracts were washed once with 25 milliliters of aqueous 3M HCl, followed by 25 milliliters of H$_2$O. The organic phase was further washed with saturated K$_2$CO$_3$ solution (5×25 milliliters), followed by 25 milliliters of H$_2$O, and finally 25 milliliters of brine. The organics were concentrated to a total volume of approximately 15-20 milliliters and 40 milliliters of heptane was added with stirring. Shortly after the addition of heptane, the product began to precipitate from solution as a yellow solid. The suspension was stirred for an hour at room temperature, cooled to 0-5° C., and stirred an additional 1 hour cold. The crude product was filtered and the cake washed once with cold (0-10° C.) 50/50 (v/v) of MTBE/heptane followed by two heptane washes. The product was dried a short time on the filter to give 5.83 grams of crude fenretinide that contained a small amount of solvent (99.0% pure by area percent). The crude product was dissolved in 40 milliliters of warm ethanol and heated to 70-78° C. with stirring. Water (12 milliliters) was added at >70° C. and the heat removed. Upon cooling the product began to crystallize as a yellow solid. The suspension was stirred for 30-45 minutes at <30° C. and further cooled to 0-5° C. for an additional 30 minutes. The product was isolated via filtration and washed two times with 20 milliliters of cold 60/40 (v/v) ethanol/H$_2$O. The product was dried at 40 to 45° C. overnight to yield 2.84 grams of fenretinide (43% overall yield from retinoic acid, 99.5% pure by area percent HPLC) as a yellow solid.

Thus, the invention provides a simpler and less expensive method for preparing amides of retinoic acid, such as fenretinide which is currently in clinical trials for the treatment of childhood brain cancer.

Although the present invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A process for preparing an amide of retinoic acid, the process comprising:
   (a) reacting a retinoic acid having the formula:

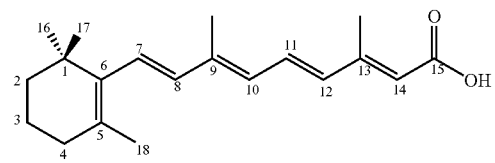

or isomers thereof with a compound having a formula selected from:

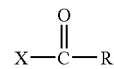

and

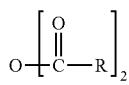

wherein R is alkyl or aryl or alkoxy, and X is a halogen, to produce an intermediate having the formula:

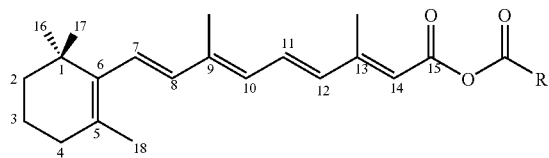

and (b) reacting the intermediate with 4-aminophenol to produce an amide of retinoic acid having the formula:

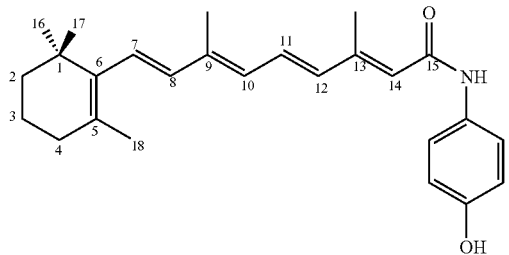

or isomers thereof.

2. The process of claim 1 wherein:
the retinoic acid is all-trans-retinoic acid.
3. The process of claim 1 wherein:
the retinoic acid is 9-cis-retinoic acid.
4. The process of claim 1 wherein:
the retinoic acid is 13-cis-retinoic acid.
5. The process of claim 1 wherein:
X is chlorine.
6. The process of claim 1 wherein:
R is trimethylalkyl.

7. The process of claim 1 wherein:
R is selected from —C(CH$_3$)$_3$ and —C(CH$_3$)$_2$CH$_2$CH$_3$.
8. The process of claim 1 wherein:
R is selected from —OCH(CH$_3$)$_2$ and —OCH$_2$CH(CH$_3$)$_2$.
9. The process of claim 1 wherein:
the compound is trimethylacetyl chloride.
10. The process of claim 1 wherein:
the compound is 2,2-dimethylbutyryl chloride.
11. The process of claim 1 wherein:
the compound is isobutylchloroformate.
12. The process of claim 1 wherein:
the compound is isopropylchloroformate.
13. The process of claim 1 wherein:
step (a) comprises reacting the retinoic acid and the compound in the presence of a solvent selected from the group consisting of ethyl acetate, t-butyl methyl ether, 2-methyltetrahydrofuran, toluene, acetonitrile, methylene chloride, dimethyl formamide, tetrahydrofuran, pyridine, and mixtures thereof.
14. The process of claim 1 wherein:
step (a) comprises reacting the retinoic acid and the compound in the presence of an amine base.
15. The process of claim 1 wherein:
step (a) comprises reacting the retinoic acid and the compound in the presence of base selected from the group consisting of triethylamine, diisopropylethylamine, N-methylmorpholine, pyridine, 1,8-diazabicyclo[5.4.0]undec-7-ene, metal carbonates, metal bicarbonates and mixtures thereof.
16. The process of claim 1 wherein:
step (b) comprises reacting the intermediate with 4-aminophenol in the presence of a solvent selected from the group consisting of pyridine, dimethyl formamide, dimethylacetamide, and mixtures thereof.
17. The process of claim 1 wherein:
the amide is prepared in a yield of at least 70%.
18. The process of claim 1 wherein:
the amide is prepared in a yield of at least 85%.
19. The process of claim 1 wherein:
step (a) comprises reacting the retinoic acid and the compound in the temperature range of 0-10° C., and
step (b) comprises reacting the intermediate with 4-aminophenol in the temperature range of 0-10° C.

* * * * *